United States Patent

Solazzi

[11] Patent Number: 6,009,766
[45] Date of Patent: Jan. 4, 2000

[54] APPARATUS AND METHOD FOR AFFIXING THIN FILM MATERIAL TO SAMPLE CUP USED IN X-RAY SPECTROSCOPY

[76] Inventor: Monte J. Solazzi, 1904 SW. Whitemarsh Way, Palm City, Fla. 34990

[21] Appl. No.: 09/145,527

[22] Filed: Sep. 2, 1998

[51] Int. Cl.[7] ..................................... B01L 3/00
[52] U.S. Cl. ................. 73/864.91; 73/863; 422/102
[58] Field of Search ........................... 73/863, 866.5, 73/863.23, 864.91, 61.55; 356/246; 422/102; 378/208; 220/276

[56] References Cited

U.S. PATENT DOCUMENTS

| | | | |
|---|---|---|---|
| 4,037,109 | 7/1977 | Hosokawa et al. | 356/246 |
| 4,575,869 | 3/1986 | Torrisi et al. | 356/246 |
| 5,451,375 | 9/1995 | Solazzi | 73/864.91 |

*Primary Examiner*—Hezron Williams
*Assistant Examiner*—Thuy Vinh Tran
*Attorney, Agent, or Firm*—Arthur L. Plevy

[57] ABSTRACT

A method for covering a sample cup for retaining a sample to be analyzed spectrochemically, the method comprising the steps of attaching a thin-film material to a substrate having a through hole to form a planar frame member, the thin-film material covering the through hole and having a patterned perforation positioned within the through hole defining an inner covering surface with diameter d1 and an outer detaching surface; disposing the planar frame member onto an open top surface of the sample cup with diameter d2 less than d1 such that the inner covering surface of the thin-film material extends across the open top surface; and depressing a portion of the planar frame member to cause detachment of the thin-film material from the substrate along the patterned perforation, and thereby causing increased tautness of the inner covering surface which extends across the open top surface.

20 Claims, 5 Drawing Sheets

APPARATUS AND METHOD FOR AFFIXING THIN FILM MATERIAL TO SAMPLE CUP USED IN X-RAY SPECTROSCOPY

FIELD OF THE INVENTION

This invention relates to an apparatus for holding specimens for spectrochemical analysis, and more particularly to an apparatus comprising a thin film material detachably coupled to a substrate, whereby a sample cup for holding the specimens engages the thin film material to cause the material to detach from the substrate and affix to the cup.

BACKGROUND OF THE INVENTION

Spectroscopy is the science where a sample substance is analyzed by means of the spectra of light the sample absorbs or emits. Technological advancements in both wavelength-dispersive (WD-XRF) and energy-dispersive (ED-XRF) X-ray fluorescence instrumentation enable the spectroscopic analysis of virtually all types of sample materials. In this technology, sample cups or sample receptacles are employed to hold or contain liquid, solid and powdered specimens. Many conventional prior art sample cups consist of four components. Components include a cell body with at least one open end; a thin film of material capable of covering the open end of the cell body; and a snap-on ring used to secure the thin film of material in place. The thin film of material encloses a sample substance within the cell body and provides a sample surface plane which is exposed to an excitation source, such as an X-ray tube, during the spectrochemical analysis. Such conventional prior art cups are exemplified by U.S. Pat. No. Des. 238,693 entitled "CELL FOR X-RAY SPECTROSCOPY OR SIMILAR ARTICLE" issued on Fib. 3, 1976 to Monte J. Solazzi; U.S. Pat. No. 4,409,854 entitled SAMPLE CUP WITH VENTING MEANS FOR USE IN X-RAY SPECTROSCOPY issued on Oct. 18, 1983 to Michael C. Solazzi; U.S. Pat. No. 4,643,033 entitled SAMPLE CUP FOR USE IN X-RAY SPECTROSCOPY issued on Feb. 17, 1987 to Monte J. Solazzi; U.S. Pat. No. 4,665,759 entitled SAMPLE CUP WITH A CANTILEVER BEAM VENTING MEANS issued on May 19, 1987 to Monte J. Solazzi; and U.S. Pat. No 4,698,210 entitled SAMPLE CUP APPARATUS FOR USE IN X-RAY SPECTROSCOPY EMPLOYING SELECTIVELY OPERATED VENTING MEANS issued on Oct. 6, 1987 to Michael C. Solazzi. All of the above patents are assigned to Chemplex Industries, the assignee herein.

During spectrochemical analysis it is essential for the surface of thin film material, which covers the opened top of the cell body, to remain planar in order to produce reliable dam. The area of the thin film material that covers the top of the cell body, is known as the sample surface plane. During the spectrochemical analysis of certain specimens that exhibit a high abrogation in air, the sample cup retaining the specimen may be placed within a vacuum or inert gas environment. Under conditions where pressure equalization is not implemented, the thin film of material covering the sample will distend or bow outwardly due to the differential in pressures between the area within the sample cup and the environment surrounding the sample cup. This places portions of the thin film of material closer to the source of excitation. This variation in distance from the sample plane to the source of excitation alters the intensity of the characteristic radiation impinging upon the sample specimen from the excitation source. Consequently, the spectrochemical analysis may produce erroneous quantitative data. For applications in a gaseous environment where pressure is greater on the outside of the sample cup than within the sample cup, the thin film of material distends or is drawn into the hollow of the sample cup providing a concave sample surface. This effect increases the distance between the sample plane and the excitation source and results in erroneous analytical data.

In order to equalize pressure and eliminate distension of the sample surface plane, some sample cups are provided with a venting means. The venting means may be activated to provide pressure equalization between the inside and outside of the cup. Other sample cup designs include a main cell component with both ends opened. This double open-ended cup allows for attachment of the thin film sheet prior to the introduction of the sample. This design is useful for applications in an environment where continuous venting is desired from the moment of sample introduction.

In the prior art, when a sheet of the thin film material is positioned over the open end of a cell body be means of the annular collar, portions of the thin film of material extend beyond the collar along the outer walls of the cell body. This excess portion of the thin film of material has a tendency to flare away from the sides of the cell body and impairs the handling of the sample cup. As such, the excess thin film material must be trimmed from the sides of the cell body in order that the sample cup may be conveniently handled.

Furthermore, in the prior art, securing the thin film of material over the open end of the cell body is a two step process. First, the annular ring must be placed over the thin film of material so as to pull the thin film of material down along the sides of the cell body. Second, the snap-on ring must be applied to secure the thin film of material into place. The two step operation causes excessive manipulation of the thin film of material which often results in the ripping of the thin film of material as the thin film of material is repeatedly stressed against the cell body.

Still further, manipulation and handling of the thin film material results in potential contamination being introduced into the specimen from such handling. Also, because thin film materials or sample support substances are generally made of a polymer composition and electrostatically charged, the prior art attachment procedure to a sample cup would cause the thin film to statically adhere to the analyst's fingers and to the sample cup. This made it cumbersome and difficult to position and attach the thin film substance while increasing the possibility of introducing contamination through extra handling.

It is therefore and object of the present invention to provide an improved apparatus and method for affixing thin film substances to sample cups which reduces or eliminates contamination and the problems associated with handling static electrically charged thin film material, while facilitating ease of attachment by eliminating the need to trim extraneous thin film material from around the cell body.

SUMMARY OF THE INVENTION

It is an object of the present invention to provide an apparatus for use in conjunction with a sample cup for placement of a thin film of material over an open surface of the sample cup for retaining a sample to be analyzed spectrochemically, the apparatus comprising a substrate having a through hole; a thin-film material coupled to the substrate and covering the through hole, the thin-film material having a patterned perforation, the patterned perforation defining an inner covering surface region and an outer detaching surface region, wherein the patterned perforation is situated within the diameter of the through hole, and wherein the inner cover surface region has an area exceeding the sample cup open surface; whereby engaging the sample cup with the apparatus such that the inner covering surface extends across the open surface, and depressing a portion of the apparatus so that the inner covering surface coacts with the open surface of the sample cup to cause detachment of the thin-film material at the patterned perforation, and increased tautness of the inner covering surface which extends across the open top surface.

It is also an object of the present invention to provide a method for covering a sample cup for retaining a sample to be analyzed spectrochemically, the method comprising the steps of attaching a thin-film material to a substrate having a through hole to form a planar frame member, the thin-film material covering the through hole and having a patterned perforation positioned within the through hole defining an inner covering surface with diameter d1 and an outer detaching surface; disposing the planar frame member onto an open top surface of the sample cup with diameter d2 less than d1 such that the inner covering surface of the thin-film material extends across the open top surface; and depressing a portion of the planar frame member to cause detachment of the thin-film material from the substrate along the patterned perforation, and thereby causing increased tautness of the inner covering surface which extends across the open top surface.

DETAILED DESCRIPTION OF THE INVENTION

Figure 1:
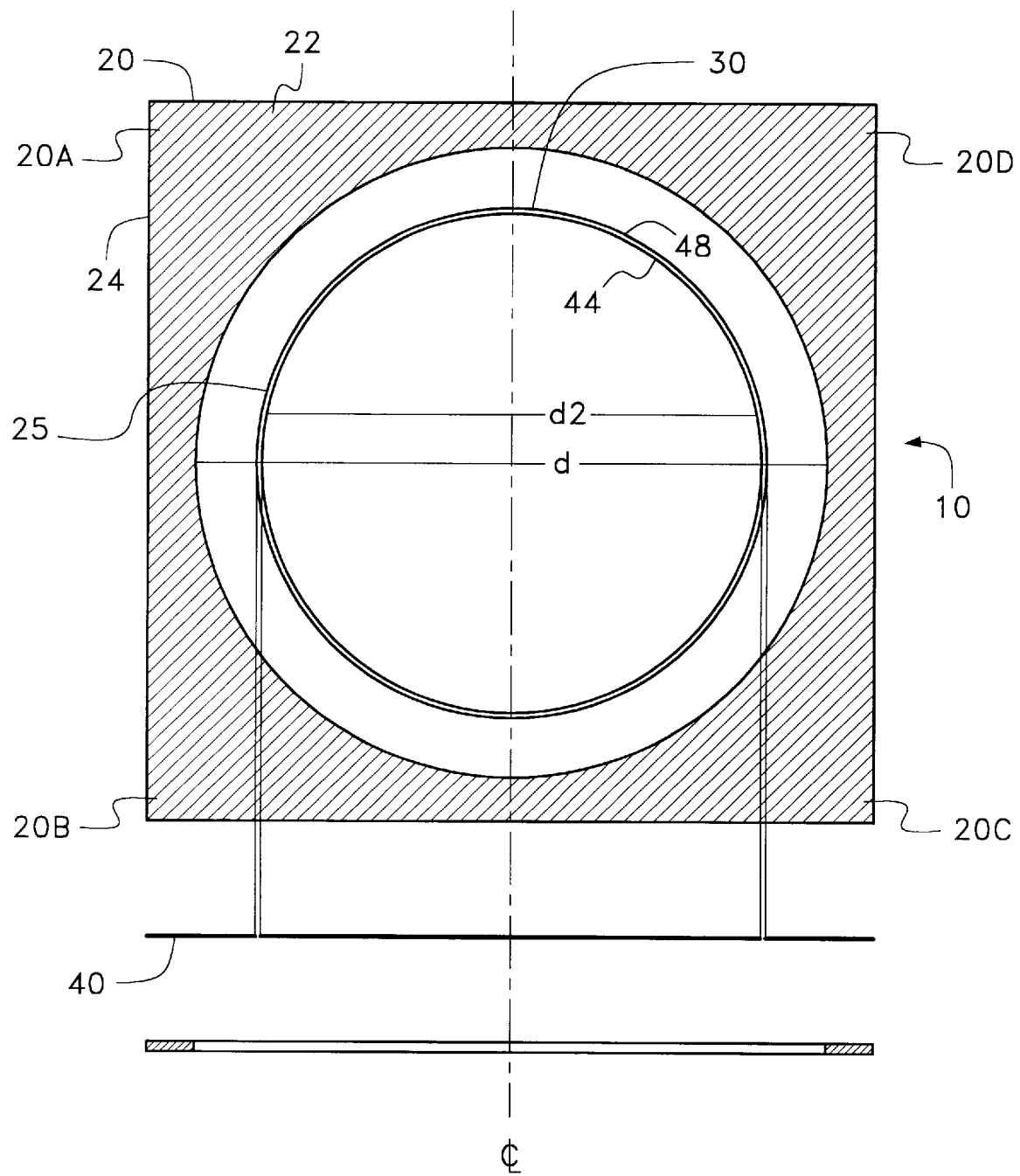
FIG. 1 is a top view of the apparatus used for affixing thin film material to a sample cup according to the present invention.

Referring now to FIG. 1, there is shown a preferred embodiment of an apparatus used in conjunction with a sample cup for placement of a thin film material over an open surface of the sample cup according to the present invention. The apparatus shown in FIG. 1 discloses a planar frame member 10 comprising a thin substrate 20 having a cavity or through hole 25. The substrate 20 is preferably shaped in the form of a square or rectangle and made of a substance of sufficient strength and durability to be handled without deformation, while being lightweight to facilitate handling and shipping. Such material may include plastic, paper, metal, or other materials having the above-mentioned properties. The substrate must also have sufficient material properties to permit attachment of a thin film material for covering the through hole.

In the preferred embodiment, the through hole 25 is circular in shape, having a diameter d. The through hole 25 extends between the upper surface 22 and the lower surface 24 opposite surface 22 of substrate 20. A thin film material such as polyester, polyamide, polycarbonate or polypropylene, is then disposed onto top surface 22 of substrate 20 in such a way that the thin film material 40 completely covers and extends across through hole 25. Note that the thin film may also be disposed on and attached to bottom surface 24. Thin film 40 includes a perforated line or area 30 which is patterned in a predetermined configuration. In the preferred embodiment, the perforation comprises a circular perforation 30, although other configurations are contemplated for conformance with the geometry of the sample cup to be used.

The circular perforation 30 thus divides the thin film into an inner surface 44 and an outer surface 48. The inner surface covering 44 is thus defined as the region interior to circular perforation 30, while outer detaching surface 48 is defined as the region of thin film material exterior to the perforation line. The geometry of the overall thin film material 40 may include a variety of shapes and sizes sufficient to cover the through hole. The thin film 40 has an overall diameter greater than the diameter of the through hole and a diameter d2 defined by the circular perforation (and associated with inner surface covering region 44) which is less than the diameter d of the through hole. Thin film 40 is then disposed onto the surface of substrate 20 and extended so that the material is taut and so that the annular perforation lies within the through hole as shown in FIG. 1. The annularly perforated thin film material is then attached to the substrate using conventional means such as an adhesive or adhesive bonding, ultrasonic bonding, or mechanically coupling the material to the substrate. As previously mentioned, the inner surface coverage region of the annular perforation is situated within the through hole in the substrate to form the frame.

Figure 2A:
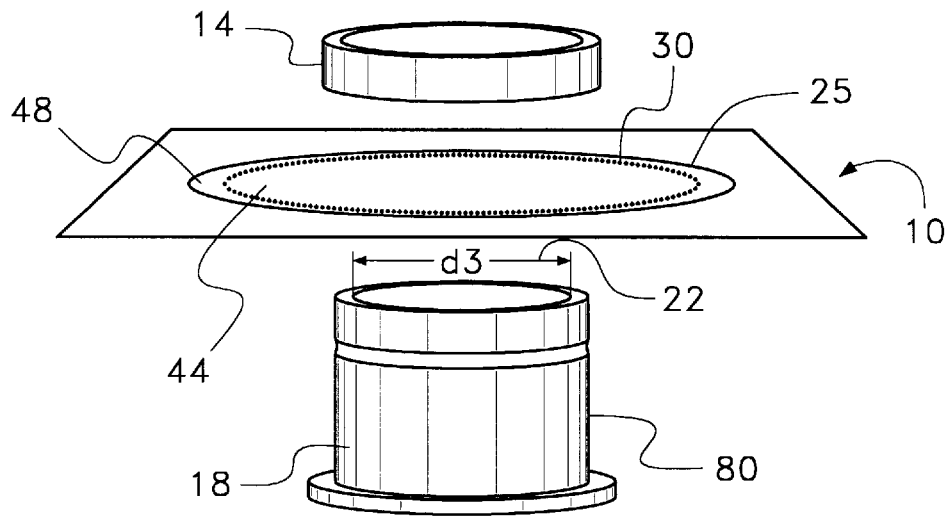
FIGS. 2A–2C illustrate the steps for using the apparatus to attach the thin film to a sample cup using a snap ring according to an embodiment of the present invention.
Figure 2B:
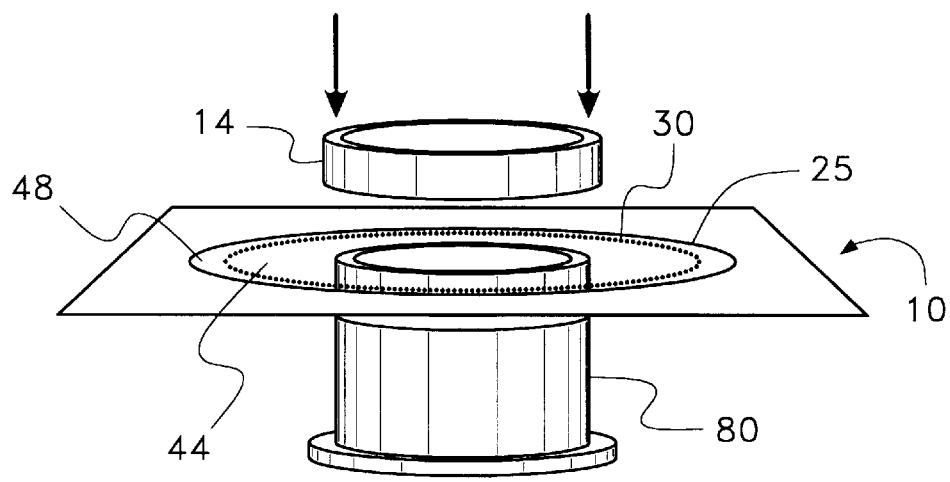
Figure 2C:
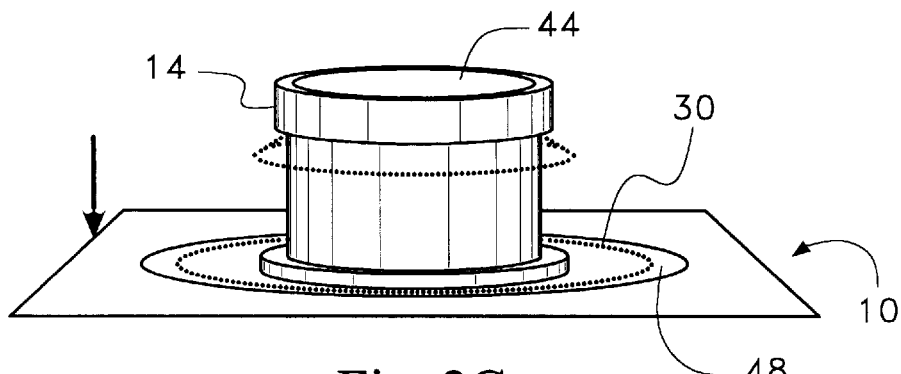

Referring now to FIGS. 2A–C, the frame 10 is then centrally placed over a sample cup 80 having an open top surface 22 and a hollow 18 interior to the cup for receiving and retaining a volume sample. Such a sample cup is disclosed in U.S. Pat. No. 5,451,375 entitled APPARATUS FOR TRIMLESS SAMPLE CUP USED IN X-RAY SPECTROSCOPY, issued Sep. 19, 1995 to Solazzi and assigned to Chemplex Industries, Inc., the assignee herein and incorporated herein by reference. As shown in FIG. 2A, the open surface 22 of sample cup 80 is of circular configuration and has a diameter d3 which is less than the diameter associated with the inner coverage surface region 44 of the thin film material. The frame member 10 is then centrally placed over the sample cup such that the inner covering surface extends over and across the open surface 22 of the cup, while the perforation 30 extends beyond the diameter of the open surface. A snap-on annular ring 14 of a conventional type having dimensions suitably compatible with sample cup 80 is then applied to the inner coverage surface region of the thin film material of frame 10, so that the frame is interposed between the snap-on ring on its top surface and the sample cup at its bottom surface. Applying downward pressure to the snap-on ring (FIG. 2B) causes detachment of the thin film material at the location of the perforation so that inner covered surface region 44 is detached from the remainder of the frame and extends completely over the top surface of the sample cup (FIG. 2C). By applying the pressure of the snap-on ring to detach the thin film material, the inner coverage surface region 44 exhibits increased tautness over the sample cup.

Alternatively, the apparatus may be applied to the sample cup without the aid of the snap-on ring or other method of thin film attachment. Instead, merely applying a small amount of force to the top surface planar frame member in a downward direction and preferably to the four opposite end regions (20A–D) of the substrate, in a substantially even manner, causes detachment of the thin film material from the substrate along the pattern perforation and increases the tautness of the inner covering surface region extending across the open top surface of the sample cup. Alternatively, application and adherence of the thin film material to the cup surface may also be accomplished by substantially even depression of only two regions of the substrate (e.g. 20A and 20C) opposite one another and displaced along a diagonal.

From the above discussion, it can be seen that the above apparatus and method provides for a taut thin film cover over the sample cup, which eliminate wrinkles in the thin film of material and provides a consistently planar sample surface. The above application also eliminates electrostatic charges associated with the handling of the thin film, since any movement or centering of the film may be accomplished by grasping the substrate portion of the frame rather than the film, thereby eliminating contact with the film material.

Figure 3:
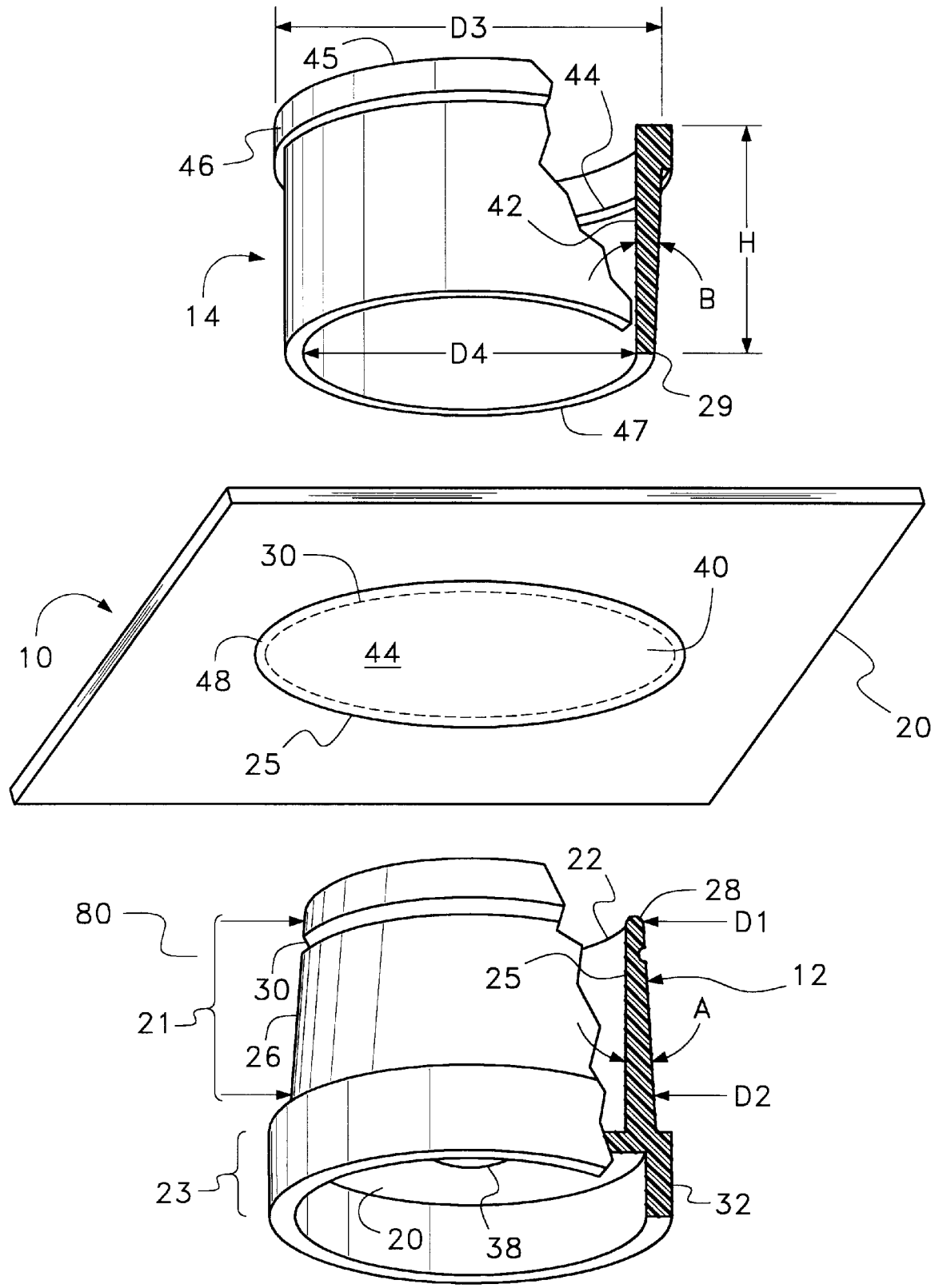
FIG. 3 is an exploded perspective view showing the details of the sample cup and apparatus and frame member apparatus according to the present invention.

As shown in FIG. 3, the sample cup 80 may be of a conventional type and may include annular collar 14 (see FIG. 3) which operates to secure the perforated sheet of thin film material over the cell body 12. The sample cap depicted in U.S. Pat. No. 5,451,375 and corresponding snap-on ring may be used in conjunction with the present frame member apparatus and will be described here briefly for completeness. For further information, and details regarding such application, the reader is directed to the above-identified patent.

As shown in FIG. 3, the cell body 12 of sample cup 80 includes a sample retaining region 21 and a reservoir region 23. The sample retaining region 21 of the cell body 12 is tubular in shape having an open end 22 and a closed end 20. The inner wall 25 of the sample retaining region 21 is generally cylindrical and extends in the vertical direction from the closed end 20 up to the open end 22. As such, the inner wall 25 defines a hollow 18, capable of retaining a sample specimen (not shown). The outside wall 26 of the sample retaining region 21 is tapered at an angle of inclination A. The outside wall 26 tapers toward the end 22 of the sample retaining region 21. As such, the outside wall 26 has a first diameter D1 at the open end 22 that is smaller than the second diameter D2 at the closed end 20 of the sample retaining region 21. The edge 28 of the outside wall 26, proximate the open end 22, is rounded. Furthermore, a continuous semicircular groove 30 is disposed in the outside wall 26 proximate the edge 28.

The taper of the outside wall 26 ends at the interface of the sample retaining region 21 and the reservoir region 23. The reservoir region 23 is comprised of a cylindrical wall 32, having a vertical inside and outside surface, that surrounds and extends below the closed end 20 of the sample retaining region 21. A venting provision 38 may be disposed within the closed end 20. The venting provision 38 may be optionally ruptured, thereby allowing the hollow 18 of the sample retaining region 21 to communicate with the reservoir region 23. As such, any sample contained within the sample retaining region 21 can be vented to the reservoir region 23 as is currently practiced in many sample cups of the prior art.

As previously described, the frame member 10 comprises a substrate 20 having a through hole 25 and a sheet of thin film material 40 attached to the substrate. The thin film extends across the through hole as a cover, and includes a perforated circular portion 30 located interior to the through hole and positioned over the open end 22 of the cell body 12. The perforated portion 30 operates to define inner coverage surface region 44 and an outer detaching surface region 48. The thin film material 40 is flexible and transparent to the radiant energy used in the spectrochemical analysis.

In the preferred embodiment, the annular collar 14 has a vertical height H that is at least as high as the sample retaining region 21 on the cell body 12. The annular collar 14 is generally tubular having first open end 45 and second open end 47. The annular collar 14 has an interior wall 42 which is tapered at an angle of inclination B that is supplementary to the angle of inclination A on the outside wall 26 of the sample retaining region 21 of the cell body 12. The interior wall 42 tapers toward the second open end 47. As such, the first inner diameter d3 of the annular collar 14, proximate the first open end 45, is larger than the second inner diameter d4, proximate the second open end 47. The interior wall 42 has a rounded edge 29 proximate the second open end 47 that faces the interior of the annular collar 14. A continuous semicircular protrusion 44 extends inwardly from the interior wall 42 proximate the first end 45 of the annular collar 14. A lip extension 46 is disposed on the exterior of the annular collar 14. The lip extension 46 facilitates the handling and the alignment of the overall sample cup 10 when assembled and placed within spectroscopic instrumentation.

Figure 4:
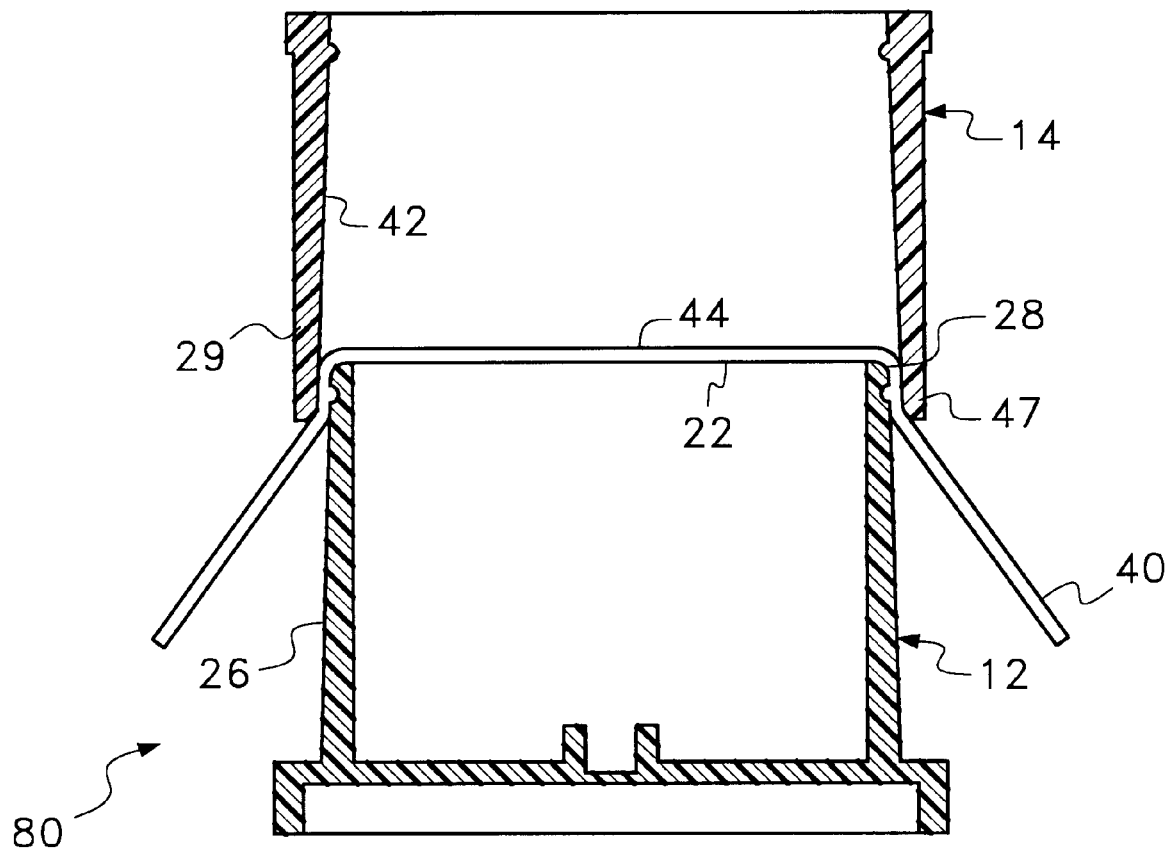
FIG. 4 is a cross sectional view of the sample cup shown in FIG. 3 in a partially assembled configuration.
Figure 5:
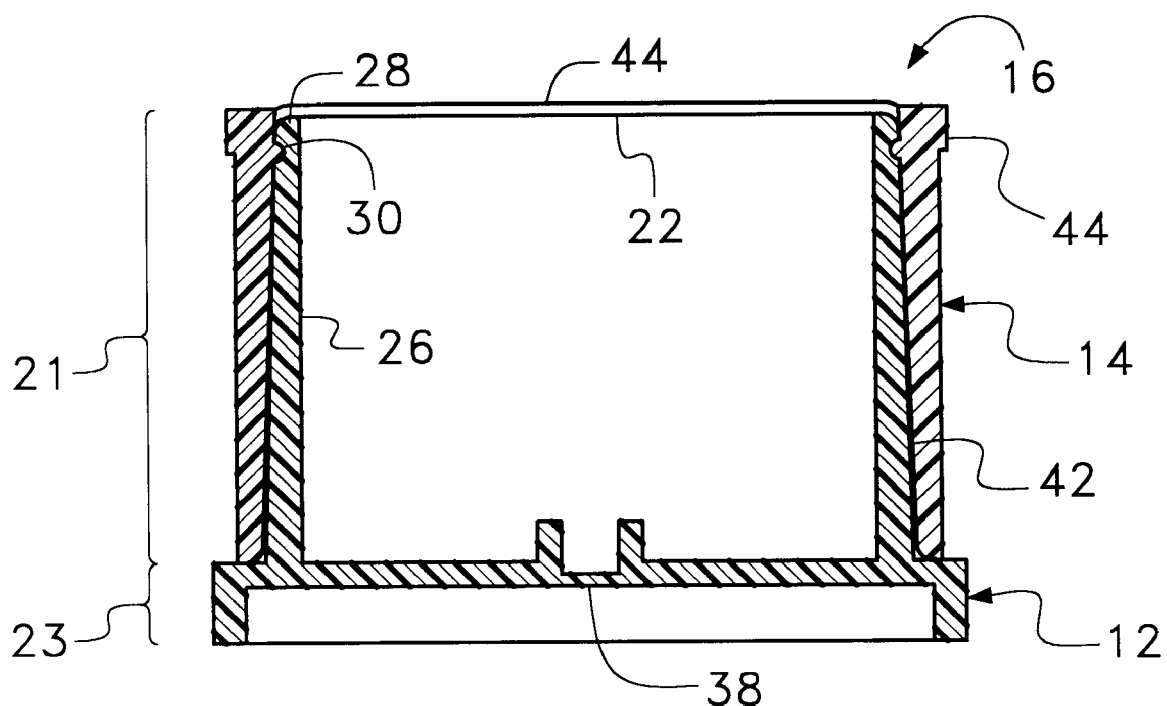
FIG. 5 is the cross sectional view of the sample cup shown in FIGS. 3 and 4 in an assembled configuration.

Referring to FIGS. 2C and 4, it can be seen that as the annular collar 14 is advanced over the cell body 12, the thin film becomes detached from the rest of the frame under the force of the downwardly moving ring along the perforation. A portion of the thin film material from the inner surface region becomes pinched between the outside wall 26 of the cell body 12 and the interior wall 42 of the annular collar 14. As such, as soon as the second open end 47 of the annular collar 14 passes the open end 22 of the cell body 12, an interference fit occurs between the annular collar 14, thin film material 40 and cell body 12. Consequently, the inner coverage surface region 44 of the thin film material 40 is immediately pulled taut across the open end 22 of cell body 12. As the annular collar 14 is further advanced along the cell body 12, the thin film material is then pulled taut over the edge 28 of the outside wall 26 on the cell body 12. The rounded shape of the edge 28 prevents the thin film material from being torn by the cell body 12. Similarly, as the annular collar 14 is advanced, the thin film material is pulled across the edge 29 of the interior wall 42. The rounded shape of the edge 29 prevents the thin film material from being torn by the annular collar 14.

As the annular collar 14 is advanced along the cell body 12, the interference fit between the interior wall 42 of the annular collar 14, the thin film material and the outside wall 26 of the cell body 12 increases due to the tapered shapes of both the interior wall 42 and the outside wall 26. As the forces of the interference fit increase, the tautness applied to the thin film material increases, thereby eliminating any folds or wrinkles in the portion of the thin film material covering the open end 22 of the cell body 12.

Referring to FIG. 3, it can be seen that the annular collar 14 completely engages the entire length of the sample retaining region 21 of the cell body 12 when the sample cup 10 is fully assembled. Assembly of the sample cup 10 is completed once the annular collar 14 is advanced far enough over the cell body 12 so that the semicircular protrusion 44 on the interior wall 42 of the annular collar 14 fits into the semicircular groove 30 on the outside wall 26 of the sample retaining region 21. Completion of assembly is indicated by a characteristic "snap" as the semicircular protrusion 44 coacts with the semicircular groove 30.

Once the sample cup 10 is assembled, the thin film material is drawn tightly over the open end 22 of the cell body 12. The thin film material creates a seal over the edge 28 of the cell body 12 which is impermeable to the sample contained therein. The interference fit between the tapered interior wall 42 of the annular collar 14 and the tapered outside wall 26 of the sample retaining region 21 of the cell body 12 occurs for the entire length of the annular collar 14. This prevents any loosening of the thin film material that covers the opened end 22 of cell body 12. As such, the thin film material will remain taut over the open end 22, creating a wrinkle-free sample surface plane for the spectro-chemical analysis.

It will be understood that the present invention apparatus affixing this film to sample cups described herein are exemplary and that a person skilled in the art may make many variations and modifications to the described embodiment utilizing functionally equivalent components to those described. As such, variations and modifications, including differing physical geometries, proportions and materials are intended to be included within the scope of the invention as defined in the appended claims.

What is claimed is:

1. An apparatus for mounting a thin-film of material across an open end of a sample cup, said thin film for retaining a sample to be analyzed spectrochemically, said apparatus comprising:

a substrate having a through hole;

a thin film material bonded to said substrate and covering said through hole, said thin film material having a perforated line of weakness defining said thin film material into an inner region and an outer region, said line of weakness situated within said through hole;

wherein, application of said apparatus over an open end of a sample cup so that said inner region of said thin film material engages the sample cup and extends across the open end thereof causes said inner region to detach from said outer region of said thin film material thereby separating said apparatus from said inner region of said thin film material.

2. The apparatus according to claim 1, wherein said perforated line of weakness is circular.

3. The apparatus according to claim 1, wherein said through hole is circular.

4. The apparatus according to claim 1, wherein said substrate comprises a plastic.

5. The apparatus according to claim 1, wherein said substrate comprises a metal.

6. The apparatus according to claim 1, wherein said thin film material comprises polymide.

7. The apparatus according to claim 1, wherein said thin film material is selected from the group consisting of polyester, polymide, polycarbonate, and polypropylene.

8. The apparatus according to claim 1, wherein said thin film material is bonded to said substrate by ultrasonic bonding.

9. The apparatus according to claim 1, wherein said thin film material is bonded to said substrate by an adhesive.

10. A method for mounting a thin film of material across an open end of a sample cup used for retaining a sample to be analyzed spectrochemically, said method comprising the steps of:

providing a planar frame member having a through hole and a thin film material bonded thereto so that said thin film material covers said through hole, said thin film material having a perforated line of weakness positioned within said through hole, said perforated line of weakness defining said thin film material into an inner region and an outer region;

placing said planar frame member onto an open end of a sample cup of so that said inner region extends across said open end of said sample cup; and simultaneously tautening said inner region of said thin film material and detaching said inner region of said thin film material from said outer region of said thin film material along said perforated line of weakness to separate said planar flame member from said sample cup.

11. The method according to claim 10, wherein said through hole is circular.

12. The method according to claim 10, wherein said planar frame member is selected from the group consisting of plastic, metal, and paper.

13. The method according to claim 10, wherein said thin film material is selected from the group consisting of polyester, polymide, polycarbonate, and polypropylene.

14. The method according to claim 10, wherein said perforated line of weakness is circular.

15. The method according to claim 10, wherein said simultaneous tautening and detaching step includes the steps of:

positioning a snap-on ring on said inner region of said thin film material;

depressing said snap-on ring to simultaneously tauten said inner region of said thin film material and detach said inner region of said thin film material from said outer region of said thin film material along said perforated line of weakness to separate said planar frame member from said sample cup.

16. The method according to claim 10, wherein said simultaneous tautening and detaching step includes the step of depressing a portion of said planar frame member to simultaneously tauten said inner region of said thin film material and detach said inner region of said thin film material from said outer region of said thin film material along said perforated line of weakness to separate said planar frame member from said sample cup.

17. The method according to claim 10, wherein said thin film material is adhesively bonded to said planar frame member.

18. The method according to claim 10, wherein said thin film material is ultrasonically bonded to said planar frame member.

19. An apparatus for mounting a thin film of material across an open end of a sample cup, said thin film for retaining a sample to be analyzed spectrochemically, said apparatus comprising:

a substrate having a through hole;

a thin film material bonded to said substrate and covering said through hole, said thin film material having a perforated line of weakness defining a thin film inner region situated within said through hole.

20. The apparatus according to claim 19, wherein said thin film material is selected from the group consisting of polyester, polymide, polycarbonate, and polypropylene.

* * * * *